United States Patent
Gerty (10) Patent No.: US 9,594,067 B2
(45) Date of Patent: *Mar. 14, 2017

(54) SYSTEMS AND METHODS FOR DETERMINING THE QUANTITY OF A COMBUSTION PRODUCT IN A VEHICLE EXHAUST

(71) Applicant: PACCAR Inc, Bellevue, WA (US)

(72) Inventor: Michael Gerty, Bellingham, WA (US)

(73) Assignee: PACCAR Inc, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/608,050

(22) Filed: Jan. 28, 2015

(65) Prior Publication Data

US 2015/0142335 A1 May 21, 2015

Related U.S. Application Data

(63) Continuation of application No. 13/835,610, filed on Mar. 15, 2013, now Pat. No. 8,966,880.

(51) Int. Cl.
*F01N 3/00* (2006.01)
*G01N 33/00* (2006.01)
(Continued)

(52) U.S. Cl.
CPC ....... *G01N 33/0037* (2013.01); *F01N 3/0231* (2013.01); *F01N 9/005* (2013.01);
(Continued)

(58) Field of Classification Search
USPC .. 60/274, 276, 285, 295, 297, 299, 301, 311
See application file for complete search history.

(56) References Cited

U.S. PATENT DOCUMENTS 7,299,626 B2 11/2007 Barasa
7,451,593 B2 11/2008 Nagaoka
(Continued)

FOREIGN PATENT DOCUMENTS

JP 2009-293412 A 12/2009
WO 02/33232 A2 4/2002
(Continued)

OTHER PUBLICATIONS

Official Action mailed Nov. 16, 2015, issued in related Canadian Application No. 2,904,884, filed Mar. 6, 2014, 5 pages.
(Continued)

*Primary Examiner* — Binh Q Tran
(74) *Attorney, Agent, or Firm* — Christensen O'Connor Johnson Kindness PLLC (57) ABSTRACT

Exhaust after treatment systems for internal combustion engine powered vehicles are provided. One system includes logic in the form of one or more routines implemented by one or more of the system's components for determining the quantity of $NO_2$ present in the exhaust that exits an oxidation catalyst, such as a diesel oxidation catalyst (DOC), without the use of an $NO_2$ sensor. Results from such a determination may then be used to estimate the amount of soot present in the particulate filter. This estimated value of soot present in the particulate filter can then be subsequently used to determine when the particulate filter should be actively regenerated.

16 Claims, 5 Drawing Sheets

(51) Int. Cl.
  *F01N 11/00* (2006.01)
  *F01N 9/00* (2006.01)
  *F01N 3/023* (2006.01)
  *G01M 15/10* (2006.01)

(52) U.S. Cl.
  CPC ......... *F01N 11/00* (2013.01); *G01M 15/102* (2013.01); *F01N 2550/02* (2013.01); *F01N 2560/026* (2013.01); *F01N 2900/1402* (2013.01); *F01N 2900/1411* (2013.01); *F01N 2900/1602* (2013.01); *Y02T 10/47* (2013.01)

(56) References Cited

U.S. PATENT DOCUMENTS

| | | | |
|---|---|---|---|
| 8,225,595 B2* | 7/2012 | Garimella | B01D 53/9409 60/274 |
| 8,245,502 B2 | 8/2012 | Theis | |
| 8,409,515 B2 | 4/2013 | Ren | |
| 8,420,036 B1* | 4/2013 | Miwa | B01D 53/9409 423/213.2 |
| 8,468,806 B2* | 6/2013 | Andersson | F01N 13/009 60/288 |
| 8,596,045 B2 | 12/2013 | Tuomivaara | |
| 8,695,329 B2 | 4/2014 | Mussmann | |
| 8,713,914 B2 | 5/2014 | Schmieg | |
| 8,899,024 B2* | 12/2014 | Masaki | F01N 3/208 60/286 |
| 8,966,880 B2* | 3/2015 | Gerty | F01N 11/00 60/274 |
| 2006/0096280 A1 | 5/2006 | Zhan | |
| 2007/0130925 A1 | 6/2007 | Ueno | |
| 2007/0144146 A1 | 6/2007 | Kusatsugu | |
| 2007/0240406 A1 | 10/2007 | Zhang | |
| 2007/0271906 A1 | 11/2007 | Berke | |
| 2008/0060350 A1 | 3/2008 | Ament | |
| 2008/0083212 A1 | 4/2008 | Ament | |
| 2008/0163609 A1 | 7/2008 | Satou | |
| 2008/0202103 A1 | 8/2008 | Henderson | |
| 2008/0256928 A1 | 10/2008 | Hunter | |
| 2009/0013665 A1 | 1/2009 | Brahma | |
| 2009/0044514 A1 | 2/2009 | Brahma | |
| 2009/0188241 A1 | 7/2009 | Sugiarto | |
| 2009/0188242 A1 | 7/2009 | Williams | |
| 2009/0188243 A1 | 7/2009 | Williams | |
| 2009/0235649 A1 | 9/2009 | Zhang | |
| 2009/0288398 A1 | 11/2009 | Perfetto | |
| 2009/0308052 A1 | 12/2009 | Zhang | |
| 2010/0005784 A1 | 1/2010 | Bird | |

FOREIGN PATENT DOCUMENTS

| | | |
|---|---|---|
| WO | 2008/135805 A1 | 11/2008 |
| WO | 2010/065963 A2 | 6/2010 |
| WO | 2012/117183 A1 | 9/2012 |

OTHER PUBLICATIONS

International Search Report and Written Opinion mailed Jun. 13, 2014, issued in corresponding International Application No. PCT/US2014/021392, filed Mar. 6, 2014, 8 pages.

* cited by examiner

SYSTEMS AND METHODS FOR DETERMINING THE QUANTITY OF A COMBUSTION PRODUCT IN A VEHICLE EXHAUST

CROSS-REFERENCE TO RELATED APPLICATION

This application is a continuation of U.S. patent application Ser. No. 13/835,610, filed Mar. 15, 2013, the disclosure of which is incorporated herein in its entirety.

BACKGROUND

Internal combustion engine exhaust emissions, and especially diesel engine exhaust emissions, have recently come under scrutiny with the advent of stricter regulations, both in the U.S. and abroad. While diesel engines are known to be more economical to run than spark-ignited engines, diesel engines inherently suffer disadvantages in the area of emissions. For example, in a diesel engine, fuel is injected during the compression stroke, as opposed to during the intake stroke in a spark-ignited engine. As a result, a diesel engine has less time to thoroughly mix the air and fuel before ignition occurs. The consequence is that diesel engine exhaust contains incompletely burned fuel known as particulate matter, or "soot." In addition to particulate matter, internal combustion engines including diesel engines produce a number of combustion products including hydrocarbons ("HC"), carbon monoxide ("CO"), oxides of nitrogen ("NOx"), and oxides of sulfur ("SOx").

After treatment systems may be utilized to reduce or eliminate emissions of these and other combustion products. For example, diesel particulate filters, such as catalyzed soot filters and others, can be used to trap diesel particulate matter and reduce emissions. The collection, or loading, of soot leads to an increase in exhaust pressure, which may degrade engine performance. To remove the particulate matter, the particulate filter can be passively regenerated by the presence of $NO_2$ in the exhaust. Additionally, particulate filters may undergo active regeneration to eliminate trapped diesel particulate matter by adding external energy into the exhaust stream, thereby raising the temperature of the particulate filter up to approximately 400 degrees Celsius with a fuel-borne catalyst and up to 600 degrees Celsius without a fuel-borne catalyst.

However, excessive regeneration of the particulate filter consumes additional fuel and can increase the rate of wear on the after treatment system. In that regard, it may be advantageous to vary when a particulate filter is regenerated to reduce fuel consumption and extend after treatment system usable life.

Thus, there is a need for one or more metrics for accurately estimating particulate loading of particulate filters or soot filters.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with aspects of the present disclosure, a system is provided for determining an amount of $NO_2$ exiting an oxidation catalyst of an exhaust after treatment system. The system includes a space velocity generator configured to generate the space velocity of an oxidation catalyst as a function of oxygen concentration present in the exhaust entering the oxidation catalyst, an $NO_2$ equilibrium generator configured to generate a value indicative of the $NO_2$ equilibrium of the exhaust, an $NO_2$ equilibrium fraction generator configured to obtain a $NO_2$ equilibrium fraction, and an $NO_2$ exit generator configured to generate a value indicating the quantity of $NO_2$ exiting the oxidation catalyst based on the value indicative of the $NO_2$ equilibrium of the exhaust and the $NO_2$ equilibrium fraction.

In accordance with another aspect of the present disclosure, a method is provided for determining an amount of $NO_2$ exiting an oxidation catalyst of an exhaust after treatment system. The method includes measuring an amount of $NO_x$ present in a stream of exhaust prior to introduction into an oxidation catalyst, determining an amount of NO in the $NO_x$, and determining an amount of $NO_2$ exiting the diesel oxidation catalyst as a function of space velocity and temperature. In some embodiments, the determined amount of $NO_2$ and the space velocity are dependent on the level of oxygen present in the $NO_x$.

In accordance with another aspect of the present disclosure, a computer implemented method is provided for determining an amount of $NO_2$ exiting an oxidation catalyst of an exhaust after treatment system. The method includes obtaining a bed temperature of the oxidation catalyst, calculating the space velocity (SV) of the oxidation catalyst, normalizing the space velocity (SV) as a function of oxygen concentration present in the exhaust, obtaining an $NO_2$ equilibrium fraction as a function of bed temperature and normalized SV, determining an $NO_2$ equilibrium, and calculating an amount of $NO_2$ exiting the oxidation catalyst based on the $NO_2$ equilibrium determination and the obtained $NO_2$ equilibrium fraction.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The detailed description set forth below in connection with the appended drawings where like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed. Similarly, any steps described herein may be interchangeable with other steps, or combinations of steps, in order to achieve the same or substantially similar result.

The following description sets forth one or more examples of exhaust after treatment systems for internal combustion engine powered vehicles and methods therefor. In some embodiments, logic in the form of one or more routines implemented by one or more components of the exhaust after treatment systems is disclosed. Examples of such routines set forth one or more methods for determining the quantity of $NO_2$ present in the exhaust that exits an oxidation catalyst, such as a diesel oxidation catalyst (DOC), without the use of an $NO_2$ sensor. In particular, since $NO_2$ sensors are not presently used on vehicles due to their complexity and expense, methods are needed for determining the amount of $NO_2$ in the exhaust at various stages of the after treatment system from other measurable and/or known operating parameters of the engine/after treatment system. The results from the methods described herein may then be used to estimate the amount of soot present in the particulate filter. This estimated value of soot present in the particulate filter can then be subsequently used to determine when the particulate filter should be actively regenerated.

As will be described in more detail below, embodiments of the present disclosure utilize one or more models that determine the amount of $NO_2$ exiting an oxidation catalyst at a given time. In several embodiments of the present disclosure, the amount of $NO_2$ exiting the oxidation catalyst is based on measured or sensed conditions within the system and predictive calculations of the amount of $NO_2$ generated by the quantity of NO and $O_2$ in the exhaust gas in the presence of a catalyst. Further as will be described in detail below, embodiments of the models described herein include the effects of oxygen on the quantity of $NO_2$ exiting the oxidation catalyst. One goal of the present disclosure, among others, is to simplify the on-board calculations and/or equipment needed to determine when to actively regenerate the particulate filter.

Prior to discussing the details of various aspects of the present disclosure, it should be understood that one or more sections of the following description may be presented in terms of logic and operations that may be performed by conventional electronic components. These electronic components, which may be grouped in a single location or distributed over a wide area, generally include controllers, microcontrollers, control units, processors, microprocessors, etc. It will be appreciated by one skilled in the art that any logic described herein may be implemented in a variety of configurations, including but not limited to hardware, software, and combinations thereof. In circumstances were the components are distributed, the components are accessible to each other via communication links.

In the following description, numerous specific details are set forth in order to provide a thorough understanding of exemplary embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Figure 1:
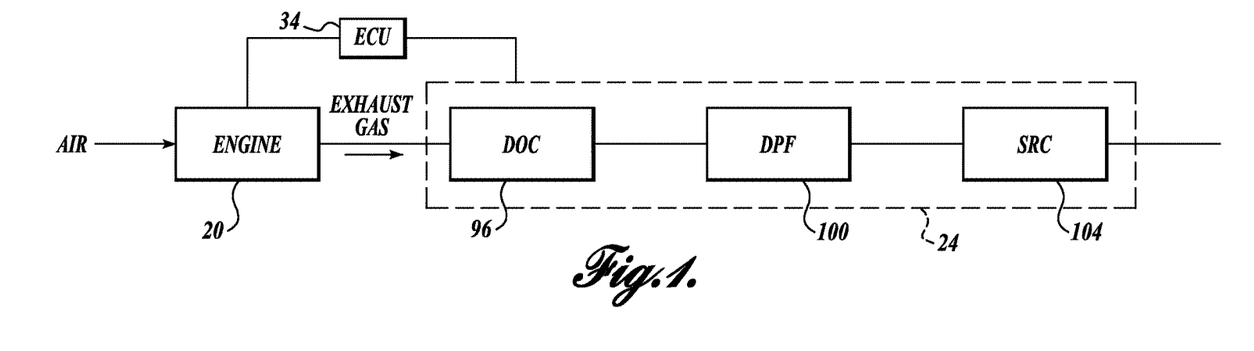
FIG. 1 is a block diagram of one example of an after treatment system coupled to an internal combustion engine in accordance with aspects of the present disclosure.
Figure 2:
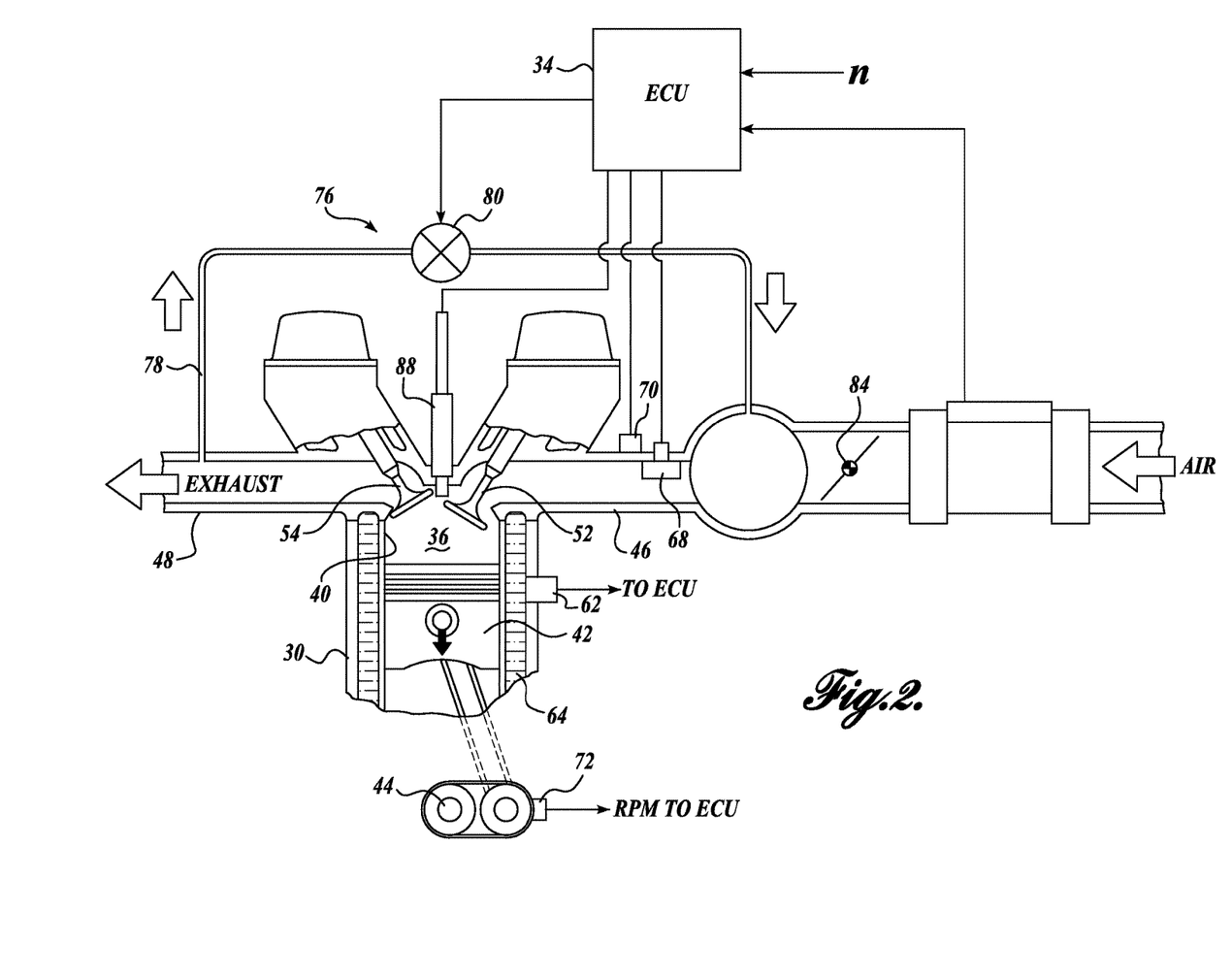
FIG. 2 is a schematic view of one example of an internal combustion engine in accordance with aspects of the present disclosure.

Referring now to FIG. 1, there is shown a block diagram of several components of a vehicle powertrain. The components include an internal combustion engine 20 in flow communication with one or more selected components of an exhaust after treatment system 24. The internal combustion engine 20, comprising a plurality of cylinders, one cylinder 30 of which is shown in FIG. 2, is controlled by electronic control unit 34, sometimes referred to as the engine control unit or ECU. As best shown in FIG. 2, the internal combustion engine 20 includes a combustion chamber 36 and cylinder walls 40 with a piston 42 positioned therein and connected to a crankshaft 44. The combustion chamber 36 is shown communicating with an intake manifold 46 and an exhaust manifold 48 via respective intake valve 52 and exhaust valve 54. In the example of FIG. 2, the internal combustion engine 20 is shown as a direct injection, diesel engine with injector 88 located to inject fuel directly into cylinder 30. Fuel is delivered to fuel injector 88 by a fuel system (not shown), including, for example, a fuel tank, fuel pump, and a high pressure common rail system. In one embodiment, the fuel injector 88 delivers fuel under control of the ECU 34. Both fuel quantity and injection timing may be adjustable.

In addition to those signals previously discussed, the ECU 34 also receives various signals from one or more sensors coupled to engine 20, including but not limited to: engine coolant temperature (ECT) from temperature sensor 62 coupled to cooling sleeve 64; a measurement of manifold pressure (MAP) from pressure sensor 68 coupled to intake manifold 46; a measurement (AT) of manifold temperature from temperature sensor 70; an engine speed signal (RPM) from engine speed sensor 72 coupled to crankshaft 44. As will be described in more detail below, one or more of these and other signals may be stored in memory of the ECU 34 or other data store.

Referring back to FIG. 1, the engine 20 is coupled to the exhaust gas after treatment system 24. As known in the art, combustion of fuel in internal combustion engines produce a number of combustion products including particulates, hydrocarbons ("HC"), carbon monoxide ("CO"), oxides of nitrogen ("$NO_x$"), including NO and $NO_2$, and oxides of sulfur ("$SO_x$"). These combustion products are referred to in both FIGS. 1 and 2 as "exhaust," which exits the exhaust manifold 48 (FIG. 2). In some embodiments, an optional turbocharger (not shown) can be coupled to engine 20 via exhaust manifold 48 and intake manifold 46. The turbocharger may include a compressor in the intake and a turbine in the exhaust coupled via a shaft.

In the embodiment shown in FIG. 2, the engine 20 may further include an exhaust gas recirculation (EGR) system 76 that recirculates the exhaust via piping 78 to the intake manifold 46. The EGR system 76 may further include an EGR control valve 80 that controls the amount of exhaust recirculation of the engine, and receives control signals from the ECU 34. Based on various engine and/or after treatment system operating characteristics, the ECU 34 can control the EGR system 76 in order to provide, for example, two or more ERG modes of operation. For example, a first EGR mode can be an EGR "off" mode wherein the control valve 80 is in a closed state, while a second ERG mode can be an ERG "on" mode wherein the control valve 80 is an open state. In some embodiments, the EGR control valve 80 can be controlled in order to vary the timing and quantity of exhaust presented to the intake manifold 46. In that regards, the ERG "on" mode can be separated into more than one mode, including ERG LOW and EGR HIGH. It will be appreciated that when the EGR system 76 is turned on, the amount of oxygen present in the exhaust decreases. In other embodiments, the engine may additionally or alternatively include a throttle 84.

Returning to FIG. 1, the exhaust after treatment system 24 optionally includes a catalyst system 96 upstream of a particulate filter 100. In the embodiment shown, the catalyst system 96 is a diesel oxidation catalyst (DOC) 96 coupled in flow communication to receive and treat exhaust from the engine 20. The DOC 96 is preferably a flow through device that includes either a honey-comb like or plate-like substrate. The substrate has a surface area that includes a catalyst. The catalyst is typically an oxidation catalyst, which may include a precious metal catalyst, such as one containing platinum, for rapid conversion of hydrocarbons (HC), carbon monoxide (CO) and nitric oxide (NO) in the engine exhaust gas. In one embodiment, the honey-comb like or plate-like substrate is coated with a platium group metal catalyst.

The oxidation catalyst 96 may also be used to supply heat in the exhaust after treatment system, wherein an exotherm is created when extra HC is reduced over the oxidation catalyst. This can be accomplished through, for example, in-cylinder injection during either or both of a power or exhaust stroke of the engine (in a direct injection engine) or any of a number of other alternatives, such as retarding injection timing, increasing EGR and intake throttling. Alternatively, hydrocarbons may be injected directly into the exhaust gas stream entering the oxidation catalyst. For example, HC from the fuel tank or from a storage vessel may be delivered to the exhaust system to generate heat for heating the particulate filter 100 for active regeneration purposes. As exhaust gas from the engine 20 traverses the catalyst, CO, gaseous HC and liquid HC (unburned fuel and oil) are oxidized. As a result, these pollutants are converted to carbon dioxide and water.

The treated exhaust gases may then proceed to the particulate filter 100, such as a diesel particulate filter (DPF) 100. The DPF 100 is utilized to capture unwanted diesel particulate matter from the flow of exhaust gas exiting engine 20. The diesel particulate matter includes sub-micron size particles found in diesel exhaust, including both solid and liquid particles, and may be classified into several fractions including: inorganic carbon (soot), organic fraction (sometimes referred to as SOF or VOF), and sulfate fraction (sometimes referred to as hydrated sulfuric acid). The DPF 100 can be manufactured from a variety of materials including but not limited to cordierite, silicon carbide, and/or other high temperature oxide ceramics. The DPF 100 also includes at least one catalyst to catalyze the oxidation of trapped particulate and/or exhaust gas components. For example, the catalyst may include a base metal/zeolite formulation with optimum $NO_x$ conversion performance in the range of approximately 200-500 degrees C., although any known oxidation catalyst may be used.

Once soot accumulation has reached a predetermined level in the DPF 100, active regeneration can be initiated by the ECU 34. As briefly discussed above, filter regeneration may be accomplished by heating the DPF 100 to a temperature that will burn soot particles at a faster rate than the deposition of new soot particles, for example, 400-600 degrees C. In one example, the DPF 100 can be a catalyzed particulate filter containing a washcoat of precious metal, such as Platinum, to lower the soot combustion temperature and also to oxidize hydrocarbons and carbon monoxide to carbon dioxide and water.

The exhaust after treatment system 24 may further include an optional Selective Catalytic Reduction (SCR) system 104. Reductant, such as aqueous urea, can be stored on-board and injected in the exhaust system upstream of an SCR catalyst. In one embodiment, the SCR catalyst includes a substrate constructed from various cermanic materials, such as titanium oxide, which can be coated with one or more active catalytic components, such as one or more oxides of base metals, zeolites, and/or precious metals.

Figure 3:
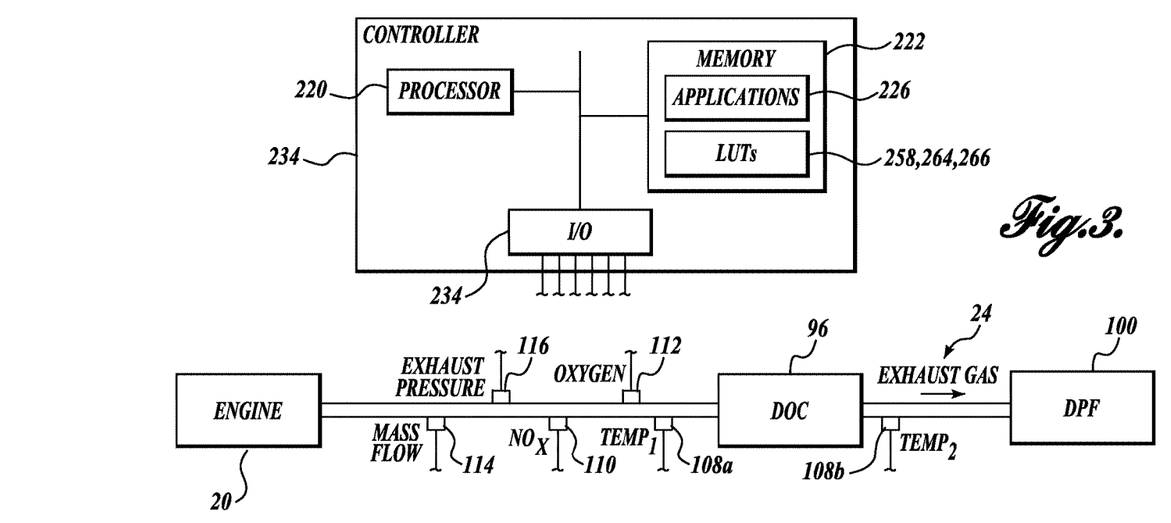
FIG. 3 is a schematic diagram of one example of an after treatment system formed in accordance with aspects of the present disclosure, the system showing one example of an electronic control unit (ECU)

Turning now to FIG. 3, additional components of the system 24 will now be described. As best shown in FIG. 3, the system 24 includes one or more sensors associated with components of the system 24. In one embodiment, the one or more sensors may include one or more temperature sensors 108. As best shown in FIG. 3, at least one temperature sensor 108 is associated with the DOC 96 for measuring the temperature of the exhaust gas as it enters the DOC 96. In other embodiments, two temperature sensors 108a and 108b may be used. In such embodiments, one sensor may be located at the entrance or upstream from the DOC 96 and another sensor may be located at the exit or downstream from the DOC 96. Information from temperature sensor(s) 108 is provided to ECU 34. An algorithm may then be used by ECU 34 to determine the operating temperature of the DOC 96, sometimes referred as the bed temperature of the DOC 96.

The one or more sensors also includes an $NO_x$ sensor 110 that senses the quantity of $NO_x$ exiting the engine 20 upstream of DOC 96, and provides to the ECU 34 a signal indicative of the amount of $NO_x$ present in the engine exhaust. Also located upstream of the DOC 96 are the oxygen sensor 112, the mass flow sensor 114, and a pressure sensor 116. For example, an oxygen sensor 112 may be positioned in fluid communication with the flow of exhaust gas exiting the engine 20, upstream of the DOC 96. The oxygen sensor 112 is preferably a universal exhaust gas oxygen sensor or lambda sensor, but could be any type of oxygen sensor. The oxygen sensor 112 is connected with ECU 34 and generates electric signals that are indicative of the amount of oxygen contained in the flow of exhaust gas. In other embodiments, the $NO_x$ sensor 110 may be of the type that also measures the quantity of oxygen contained in the exhaust gas, such as a $NO_x$ sensor currently available from Bosch.

Similar to the oxygen sensor 112 and/or $NO_x$ sensor 110, the mass flow sensor 114 and a pressure sensor 116 may also be positioned in fluid communication with the flow of exhaust gas exiting the engine 20, upstream from DOC 96. The mass flow sensor 114 and a pressure sensor 116 are connected to the ECU 34 and generate electric signals that are indicative of the mass flow rate and pressure of the exhaust gas. Signals generated by the aforementioned sensors, among others, are stored in memory of the ECU 34 or other data store(s) and may be utilized by one or more $NO_2$ determination applications, as will be described in more detail below.

Figure 5:
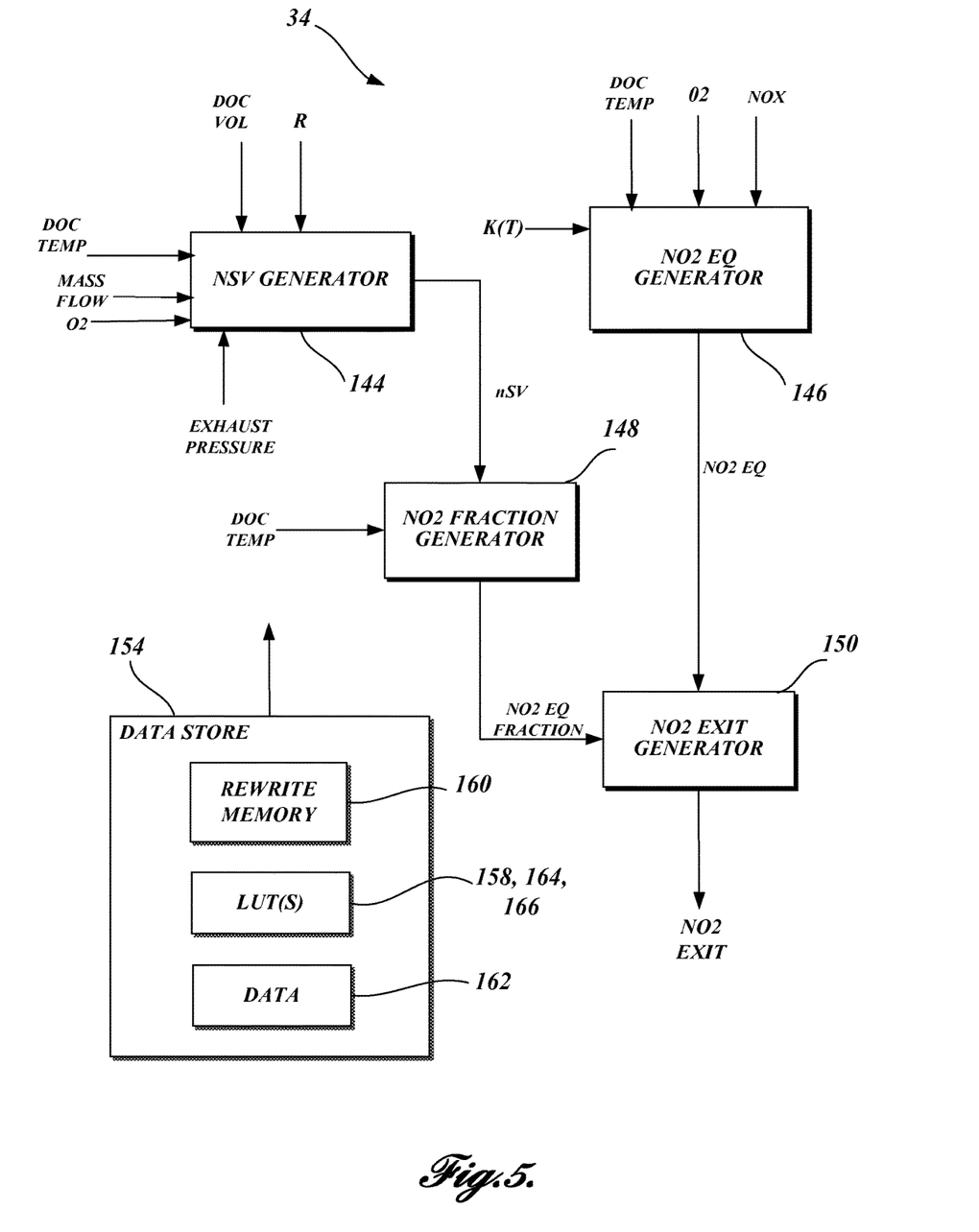
FIG. 5 is a block diagram on another example of an electronic control unit (ECU) formed in accordance with aspects of the present disclosure.

Referring now to FIG. 5, there is illustrated a functional block diagram of one example of the ECU 34. It will be appreciated that the ECU 34 can be implemented in a variety of hardware, software, and combination hardware/software configurations, for carrying out aspects of the present disclosure. It will be appreciated that the functions carried out by the ECU 34 related to the after treatment of exhaust may be alternatively carried out by a discrete controller associated with the after treatment system 24 or integrated or associated with another one or more controllers of the vehicle, such as the engine control module, among others.

Figure 4:
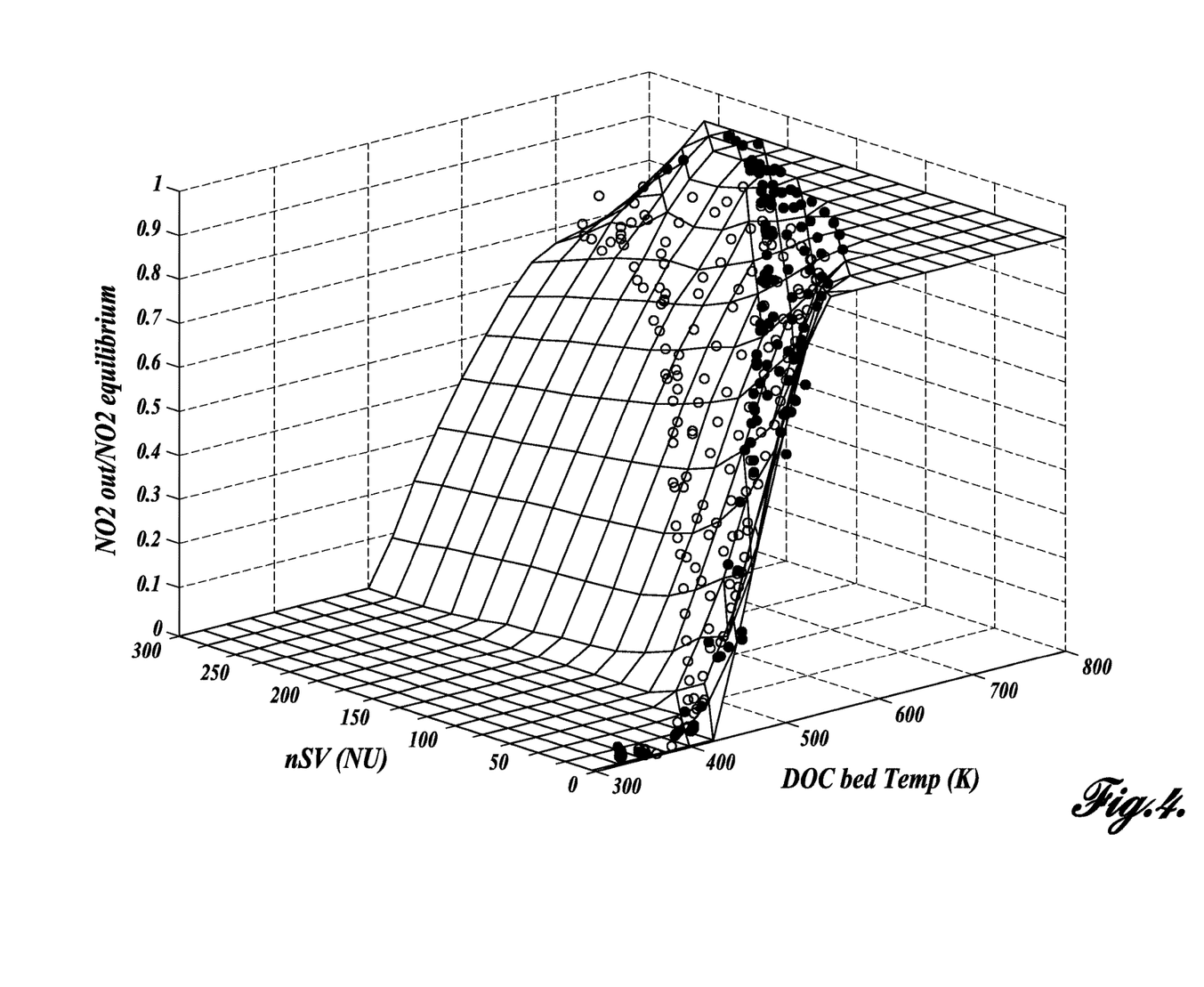
FIG. 4 is one graphical example of a multi-dimensional look up table (LUT) formed in accordance with aspects of the present disclosure.

In the embodiment shown in FIG. 5, the ECU 34 may include, but is not limited to, an nSV generator 144, an $NO_2$ EQ generator 146, an NO2 EQ Fraction generator 148, and an NO2 Exit generator 150. The ECU 34 may receive data from one or more data stores 154. In one embodiment, the one or more data stores 154 may include a $NO_2$ fraction LUT 158, a rewriteable memory section 160, and data 162, such as the exhaust gas constant (R), $NO_2$ equilibrium constant, K(t), the volume of the DOC 96, etc. In some embodiments, the LUT 158 is a multi-variable LUT, and may be generated from empirically derived data as a function of nSV and DOC bed temperature. Accordingly, with known nSV and DOC bed temperature values, the LUT 158 is capable of outputting a value representing an $NO_2$ equilibrium fraction. The NO2 equilibrium fraction represents the amount, as a fraction or a percentage (less than one) of the reaction of NO and $O_2$ that has moved to equilibrium (resulting in $NO_2$). One graphical example of the LUT 158 is shown in FIG. 4. To ease the calculations made by the ECU 34, the one or more data stores 154 in some embodiments may also include LUTs 164 and 166 that include data in the form of the square root of the $NO_2$ equilibrium constant, K(t), as a function of bed temperature of the DOC 96, and the square root of the $O_2$ fraction, respectively.

Still referring to FIG. 5, the nSV generator 144 determines the space velocity of the engine exhaust through the DOC 96 as a function of exhaust oxygen, referred to herein as nSV. Standard space velocity (SV) is equal to the volume of exhaust flow per volume of the DOC 96. As such, nSV can be determined with data from one or more sensors 108, 112, 114, 116, including mass flow rate and pressure of the exhaust, the bed temperature of the DOC 96, and the percentage of oxygen present in the exhaust, in addition to data stored in memory section 160, including the gas constant (R) of the exhaust, the volume of the DOC 96, and/or the like.

In one embodiment, the space velocity (SV) may be calculated from the following equation.

$$SV = Volume_{exhaust}/Volume_{catalyst}; \text{ where}$$

$$Volume_{exhaust} = Mass\ Flow\ Rate_{exhaust}/Density_{exhaust};\ \text{and}$$

$$Density_{exhaust} = Pressure_{exhaust}/R_{exhaust} \times Temperature_{exhaust} \quad (1)$$

In one embodiment, nSV may be calculated from the results of equation (1) above with the following equation.

$$nSV = SV/O_{2exhaust} \quad (2)$$

The $NO_2$ EQ generator 146 determines the amount of $NO_2$ that would be present in the exhaust exiting the DOC if equilibrium conditions were present. In some embodiments, $NO_2$ equilibrium can be calculated with data from one or more sensors 108, 110, 112, including the DOC bed temperature, the percentage of oxygen present in the exhaust, and the quantity (in ppm) of $NO_x$ of the exhaust, in addition to data stored in memory section 160, including the nitrogen dioxide equilibrium constant, K(t), and/or the like.

In one embodiment, the amount of $NO_2$ at equilibrium can be calculated by the following equation.

$$K(t) = [NO_2]^2/[NO]^2[O_2], \text{ where } NO_x = NO_2 + NO; \quad (3)$$

Solving for $NO_2$ and substituting $(NO_x - NO_2)$ for NO results in equation (4).

$$NO_2 = [NO_x][O_2]^{1/2}[K(t)]^{1/2}/[1+[O_2]^{1/2}[K(t)]^{1/2}] \quad (4)$$

For ease of calculation, in one embodiment the square root of the equilibrium constant, K(t), may be obtained from a LUT 164 stored in data store 154. Likewise, in one embodiment the square root of the $O_2$ percentage may be obtained from the LUT 166 stored in date store 154. Other embodiments may include configurations of hardware and/or software for easily computing $NO_2$ from equation (4), as described in more detail below.

With the results of the nSV generator 144 and DOC temperature from sensor 108, the NO2 EQ fraction generator 148 outputs the $NO_2$ equilibrium fraction with the use of the LUT 158. Next, with the outputs of both the $NO_2$ EQ fraction generator 148 and the $NO_2$ EQ generator 146, the $NO_2$ exit generator 150 determines the quantity of $NO_2$ (ppm) in the exhaust that exits the DOC, referred to herein as $NO_2$ EXIT.

In one embodiment, $NO_2$ EXIT may be calculated with the following equation.

$$NO_2\ EXIT = NO_2\ equilibrium \times NO_2\ equilibrium\ fraction \quad (5)$$

FIG. 3 depicts another embodiment of the ECU, generally designated 234, in accordance with aspects of the present disclosure. As shown in FIG. 3, the ECU 234 is depicted as a computing device that includes a processor 220, a memory 222, and I/O circuitry 224 suitably interconnected via one or more buses. In this regard, the processor 220 is configured to execute instructions and to carry out operations defined in one or more applications 226 or program modules that reside in the memory 222. The memory 222 depicted in FIG. 3 is one example of computer-readable media suited to store data, such as sensor data and program data in the form of one or more look-up tables (LUTs), and program modules that implement aspects of the disclosed subject matter. The ECU 234 is connected in communication with one or more sensors, such as sensors 108-116, etc., and other data sources via the I/O circuitry 224.

By way of example, and not limitation, computer readable media includes volatile and non-volatile and removable and non-removable memory, implemented in any method or technology capable of storing information, such as computer-readable instructions, data structures, program modules, or other data. By way of example, computer-readable media include, but are not limited to, RAM, ROM, EPROM, EEPROM, flash memory, CD-ROM, digital versatile disks (DVD), etc., or any other medium that can be used to store information for access by the processor 220.

The memory 222 may include program modules, applications, and the like that include algorithms or routines configured to perform operations that are executable by the processor 220. In that regard, the memory 222 includes an $NO_2$ determination application for determining the amount of $NO_2$ present in the exhaust gas exiting the DOC 96, referred to herein as $NO_2$ Exit. Additionally, the memory 222 may include single or multi-dimensional performance maps or look-up tables (LUTs) that are accessed by the processor 220. One such LUT includes a $NO_2$ EQ fraction LUT 258 described above with reference to FIG. 5. The LUT 258 is a multi-variable LUT, and is generated from empirically derived data as a function of nSV and DOC bed temperature. Accordingly, with known nSV and DOC bed temperature values, the LUT 258 is capable of outputting a value representing an $NO_2$ equilibrium fraction. The NO2 equilibrium fraction represents the amount, as a fraction or a percentage (less than one) of the reaction of NO and $O_2$ that moved to equilibrium (resulting in $NO_2$). The memory 222 in other embodiments may also include LUTs 264 and 266 that include data in the form of the square root of the equilibrium constant, K(t), for the formation of $NO_2$ as a function of bed temperature of the DOC 96, and the square root of the $O_2$ fraction, respectively.

The $NO_2$ determination application includes instructions that when executed by the processor 220 performs one or more functions, including one or more $NO_2$ estimation routines, as will be described in more detail below. In one embodiment, the $NO_2$ determination application is capable of polling for or receiving data from one or more system components, analyzing the data received from the system components, and/or generating control signals to be transmitted to the components of the system 24, such as starting active regeneration of the DPF via the fuel control device 80 or the like. The $NO_2$ determination application further retrieves stored data including data from one or more LUTs, including LUT 258.

During operation of the vehicle, the $NO_2$ determination application is programmed to obtain and/or calculate the space velocity of the engine exhaust through the DOC 96 as a function of exhaust oxygen, referred to herein as nSV. In some embodiments, nSV can be calculated with data, including the mass flow rate and pressure of the exhaust, the bed temperature of the DOC, and the oxygen percentage of the exhaust, data stored in memory 222, including the gas constant (R) of the exhaust and the volume of the DOC, or the like. The $NO_2$ determination application may be further configured to cause the processor 120 to access the LUT 258 in memory 222 in order to obtain the $NO_2$ equilibrium fraction as a function of DOC bed temperature and the nSV calculation. The $NO_2$ equilibrium fraction indicates how far, as a fraction or percentage, the reaction of NO and $O_2$ has moved towards equilibrium (resulting in $NO_2$). The $NO_2$ determination application may further cause the processor 120 to take the results of the LUT 258, i.e., the $NO_2$ equilibrium fraction based on the DOC bed temperature and calculated nSV, and determine, $NO_2$ EXIT, the amount of $NO_2$ present in the exhaust exiting the DOC 96. This calculation may occur after application 230 causes the processor 220 to calculate the amount of $NO_2$ that would be present if equilibrium conditions were present, referred to as $NO_2$ equilibrium. In a few embodiments, $NO_2$ EXIT is the product of the $NO_2$ equilibrium fraction and $NO_2$ equilibrium.

It will be appreciated that in some embodiments, $NO_2$ equilibrium can be calculated according to equation (4) above with data from one or more sensors, including the DOC bed temperature, the oxygen percentage of the exhaust, and the quantity (in ppm) of $NO_x$ of the exhaust, data stored in memory 222, including the $NO_2$ equilibrium constant, K(t), and/or the like.

One or more routines that can be implemented within the environment described above, including engine 20 and/or exhaust after treatment system 24, will now be described. As will be appreciated by one skilled in the art, the specific routines described below in the flowcharts may represent one or more of any number of processing strategies, such as event-driven, interrupt-driven, multi-tasking, multi-threading, and the like. As such, various acts or functions illustrated may be performed in the sequence illustrated, in parallel, or in some cases omitted. Likewise, the order of processing is not necessarily required to achieve the features and advantages, but is provided for ease of illustration and description. Although not explicitly illustrated, one or more of the illustrated acts or functions may be repeatedly performed depending on the particular strategy being used.

Figure 6:
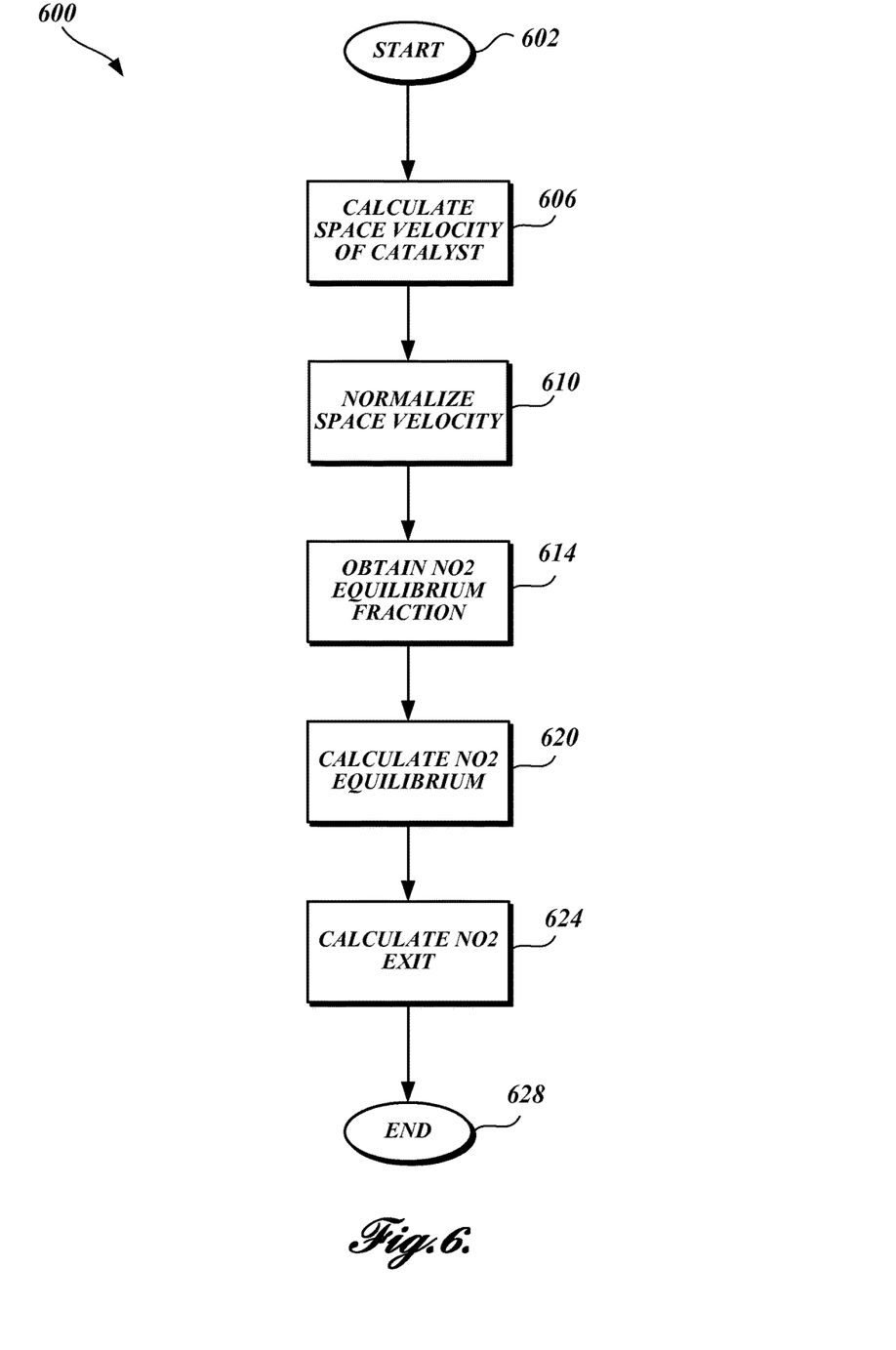
FIG. 6 is a flow diagram of one example of a method for determining the amount of $NO_2$ present in the exhaust that exits the oxidation catalyst in accordance with aspects of the present disclosure.

Referring now to FIG. 6, one example of a method 600 is set forth for determining $NO_2$ EXIT, or the amount of $NO_2$ present in the exhaust gas that exits the DOC 96. The method 600 may be implemented by one or more components, including ECUs 34, 234, etc., described above. With the results of such determination, timing and/or length of active particulate filter regeneration of the DPF can be controlled.

The method begins at block 602 and proceeds to block 606, where space velocity (SV) of the catalyst, DOC 96, is calculated. Next, at block 610, the space velocity calculation is normalized as a function of oxygen concentration present in the exhaust, resulting in normalized space velocity (nSV). From block 610, the method proceeds to block 614, where an $NO_2$ equilibrium fraction is obtained as a function of DOC bed temperature and normalized SV (nSV). In one embodiment, the $NO_2$ equilibrium fraction is obtained from a LUT, such as LUT 158, 258. Next, $NO_2$ equilibrium is calculated is block 620. The method then proceeds to block 624, where the amount of $NO_2$ EXIT is calculated from the results of the $NO_2$ equilibrium calculation and the obtained $NO_2$ equilibrium fraction. The method ends at block 628.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure.

The embodiments of the invention in which an exclusive property or privilege is claimed are defined as follows:

1. A system for determining an amount of $NO_2$ exiting an oxidation catalyst of an exhaust after treatment system, wherein the system includes an electronic controller, comprising:
   a space velocity generator configured to generate the space velocity of the oxidation catalyst;
   an $NO_2$ equilibrium generator configured to generate a value indicative of the $NO_2$ equilibrium of the exhaust;
   an $NO_2$ equilibrium fraction generator configured to obtain an $NO_2$ equilibrium fraction based on the generated space velocity; and
   an $NO_2$ exit generator configured to generate a value indicating the quantity of $NO_2$ exiting the oxidation catalyst based on the value indicative of the $NO_2$ equilibrium of the exhaust and the $NO_2$ equilibrium fraction.

2. The system of claim 1, wherein the space velocity generator is configured to calculate the space velocity of the oxidation catalyst as a function of the volume of the oxidation catalyst and the exhaust flow through the oxidation catalyst.

3. The system of claim 1, wherein the $NO_2$ equilibrium generator is configured to generate the value indicative of the $NO_2$ equilibrium of the exhaust based on one or more of oxidation catalyst temperature, equilibrium constant (K) of $NO_2$, the oxygen concentration, and quantity of $NO_x$.

4. The system of claim 1, wherein the $NO_2$ equilibrium fraction generator is further configured to obtain the $NO_2$ equilibrium fraction based on a temperature of the oxidation catalyst.

5. A method of determining an amount of $NO_2$ exiting a diesel oxidation catalyst of an exhaust after treatment system, the method comprising in an electronic control unit:

measuring an amount of $NO_x$ present in a stream of exhaust prior to introduction into an oxidation catalyst;

determining an amount of NO in the $NO_x$; and determining an amount of $NO_2$ exiting the diesel oxidation catalyst as a function of space velocity and a level of oxygen present in the $NO_x$.

6. The method of claim 5, further comprising using the determined amount of $NO_2$ exiting the diesel oxidation catalyst to estimate the amount of particulate being passively removed from a diesel particulate filter.

7. The method of claim 5, wherein the amount of NO is determined without the use of the NO sensor.

8. The method of claim 5, wherein said determining the amount of $NO_2$ exiting the diesel oxidation catalyst is a function of space velocity and temperature.

9. The method of claim 8, wherein the space velocity is dependent on the level of oxygen present in the $NO_x$.

10. The method of claim 5, further comprising using the determined amount of $NO_2$ exiting the diesel oxidation catalyst to estimate the amount of conversion in the oxidation catalyst.

11. A computer implemented method for determining an amount of $NO_2$ exiting an oxidation catalyst of an exhaust after treatment system, the method comprising in an electronic control unit:

obtaining a bed temperature of the oxidation catalyst;

calculating the space velocity of the oxidation catalyst;

obtaining an $NO_2$ equilibrium fraction as a function of bed temperature and space velocity;

determining an $NO_2$ equilibrium; and calculating an amount of $NO_2$ exiting the oxidation catalyst based on the $NO_2$ equilibrium determination and the obtained $NO_2$ equilibrium fraction.

12. The method of claim 11, wherein the $NO_2$ equilibrium fraction is obtained from a look-up table.

13. The method of claim 11, wherein the oxidation catalyst is a diesel oxidation catalyst.

14. The method of claim 11, further comprising normalizing the space velocity as a function of oxygen concentration present in the exhaust.

15. The method of claim 11, further comprising using the calculated amount of $NO_2$ exiting the diesel oxidation catalyst to estimate the amount of particulate being passively removed from a diesel particulate filter.

16. The method of claim 11, further comprising using the determined amount of $NO_2$ exiting the diesel oxidation catalyst to estimate the amount of conversion by the oxidation catalyst.

* * * * *